United States Patent [19]

Cohen et al.

[11] Patent Number: 5,149,660

[45] Date of Patent: Sep. 22, 1992

[54] DIAGNOSTIC REAGENTS RELATING TO HERPES SIMPLEX VIRUS

[75] Inventors: Gary H. Cohen, Havertown, Pa.; Roselyn J. Eisenberg, Haddonfield, N.J.

[73] Assignee: University Patents, Inc., Norwalk, Conn.

[21] Appl. No.: 712,683

[22] Filed: Jun. 10, 1991

Related U.S. Application Data

[60] Division of Ser. No. 148,285, Jan. 29, 1988, abandoned, which is a continuation of Ser. No. 463,141, Feb. 4, 1983, Pat. No. 4,762,708, which is a continuation-in-part of Ser. No. 350,021, Feb. 18, 1982, abandoned.

[51] Int. Cl.$^5$ .................. G01N 33/569; C07K 15/04; C07K 15/14
[52] U.S. Cl. .......................... 436/87; 436/86; 436/542; 424/88; 424/89; 435/7.92; 435/5
[58] Field of Search ............... 436/86, 87; 424/88, 424/89; 530/324–329, 395; 435/72, 7.91, 7.92, 536, 542

[56] References Cited

U.S. PATENT DOCUMENTS

| | | | |
|---|---|---|---|
| 4,709,011 | 11/1987 | Cohen et al. | 530/324 |
| 4,745,182 | 5/1988 | Cohen et al. | 435/5 |
| 4,762,708 | 8/1988 | Cohen et al. | 424/89 |
| 4,818,694 | 4/1989 | Watson et al. | 435/69.3 |

OTHER PUBLICATIONS

Eisenberg et al., J. Virology, 35: 428–435 (1980).
Pereira et al., Infection and Immunity, 29: 724–732 (1980).
Dix et al., Infection and Immunity, 34: 192–199 (1981).
Skinner et al., Med. Microbiol. Immunol, 169:39–51 (1980).

*Primary Examiner*—John J. Doll
*Assistant Examiner*—Robert D. Budens
*Attorney, Agent, or Firm*—Marshall, O'Toole, Gerstein, Murray & Bicknell

[57] ABSTRACT

Disclosed are diagnostic reagents for use in detection of Herpes Simplex Virus Type 1 antibodies or Herpes Simplex Virus Type 2 antibodies comprising novel Herpes Simplex Virus envelope glycoproteins gD-1 and gD-2, immunologically active fragments thereof, immunologically synthetic replicas, thereof, and specific polypeptides comprising specific amino acid sequences.

3 Claims, No Drawings

DIAGNOSTIC REAGENTS RELATING TO HERPES SIMPLEX VIRUS

CROSS-REFERENCE TO RELATED APPLICATIONS

The present invention is a divisional of co-pending U.S. patent application Ser. No. 148,285 (filed Jan. 29, 1988) which is, in turn, a continuation of U.S. Ser. No. 463,141 (filed Feb. 4, 1983 and issued Nov. 24, 1987 as U.S. Pat. No. 4,762,708) which is, in turn, a continuation-in-part of U.S. patent application Ser. No. 350,021 (filed Feb. 18, 1982 and abandoned Sep. 2, 1983).

BACKGROUND

The present invention relates generally to materials and methods for developing protective responses against Herpes simplex virus ("HSV") disease states. More particularly, the present invention relates to novel preparations of HSV envelope glycoprotein gD which, when employed as the active immunogen of vaccine compositions, provoke significantly better protection in a recipient against an HSV infection disease state than heretofore obtainable in the art. The invention also relates to immunoreactive polypeptides which duplicate or substantially duplicate amino acid sequences extant in HSV gD and to the use of such polypeptides in vaccination procedures.

Incorporated by reference herein for purposes of providing relatively current information concerning the background of the present invention is a publication of Wise, et al., "Herpes Simplex Virus Vaccines", *J. Infectious Diseases*, 136, pp. 706–711 (1977). Briefly summarized, this 1977 publication states that clinical illness caused by Herpes simplex virus, and especially the disability associated with recurrent infections, is a significant health problem that cannot be prevented at present. Alteration of the immune system by vaccination, it was thought, could potentially prevent or limit the infection upon subsequent exposure to the natural virus. Because such vaccination had proved efficacious in the control of many human diseases of viral etiology, an attempt to develop a vaccine against HSV was presented as a logical consideration. To accomplish this goal satisfactorily, it was noted that a number of attributes unique to the virus must be examined. These included the natural history, epidemiology, and severity of the disease, the various immune responses that were known to follow infection with the virus or immunization with experimental vaccines, and the possible risks associated with vaccine usage.

HSV, a large, enveloped, DNA-containing virus, was noted to cause a variety of clinical entities associated with primary infection, principally involving the skin, mucosal membranes, cornea, and nervous system. The two types of HSV—type 1 (HSV-1) and type 2 (HSV-2)—were mentioned to be distinguishable by their antigenic, biologic, and biochemical characteristics. Because HSV-1 and HSV-2 differed antigenically and because an individual could have a primary infection with either type, "type-specific" HSV vaccines were stated to be a likely requirement of any vaccine development program.

HSV was noted to have the ability to cause both "primary" and "recurrent" infections. Since the pathogenesis of primary and recurrent infections were clearly different, the rationale for development of a vaccine against these two entities was considered separately.

Natural infection with HSV was noted to bring into play many specific and nonspecific components of the immune defense system. Antibodies had been found to develop soon after primary infection, reach maximal levels within three to four weeks, and remain detectable for many years thereafter. Cellular immune responses to HSV infection were also detected in vivo by a delayed-type hypersensitivity response to the intradermal injection of viral antigens and in vitro by the many correlates of cellular immunity. The effects of the immune response induced by HSV upon subsequent infections in laboratory animals and humans were reported on. For example, mice immunized with either live or killed HSV, unlike unimmunized mice, were frequently found to be resistant to subsequent lethal challenge with HSV. In humans, it appeared that if individuals had preexisting HSV-1 antibodies, primary infection with HSV-2 tended to be milder. This observation and the data from studies of HSV disease in animals suggested that the immune response induced by HSV could have a beneficial effect on subsequent HSV infections and that, if a HSV vaccine could induce a similar immune response, it could ameliorate the clinical manifestations of primary HSV infections.

Herpes simplex viruses were then noted to characteristically persist in the host and cause recurrent infections, and the disability associated with these recurrences was described as a significant health problem. The most frequent manifestations of recurrent herpetic disease states were disclosed to involve the orofacial and genital regions and recurrent herpetic keratitis was characterized as a leading cause of blindness in the United States. Herpetic genital infections with a high incidence of subsequent recurrent episodes were noted as being recognized more frequently and being associated with significant morbidity.

The source of the virus that leads to recurrent disease was noted to be of major importance to the rationale for developing a HSV vaccine. On the basis of a variety of clinical observations, it was concluded that the virus remained dormant in nervous tissue. The isolations of HSV-1 from the trigeminal ganglia and of HSV-2 from the sacral ganglia of humans were asserted to be major steps in the further development of this concept, as were the results obtained from animal models. After extensive discussion of clinical studies of latent infections, it was generally concluded that the possibility of developing a vaccine protective against both primary infection and recurrent infection was highly remote.

HSV vaccine candidates were enumerated: live attenuated virus; inactivated whole virus; and inactivated "sub-unit" viral components. Live viral vaccines were noted to be frequently preferred over inactivated ones because the immune responses induced by live vaccines tend to be higher and of longer duration, and because live vaccines require a smaller inoculum owing to the ability of the virus to multiply in the host. The disadvantage of live viral vaccines in terms of difficulty in production and in maintenance in proper degree of attenuation were noted as were the then-preliminary studies revealing that at least HSV-2 appeared to be oncogenic in humans. Since it appeared that infectious virus was not required for the in vitro transformation of cells, this highly unfavorable risk consideration was also held to be applicable to inactivated vaccines containing viral nucleic acid. Various live and attenuated virus vaccine preparations were discussed and the conclusion was reached that none provided beneficial results sufficient to justify oncogenic risks.

The development of an inactivated vaccine containing sub-unit viral components with little or no viral DNA was therefore proposed as lessening the concern of oncogenicity. Sub-unit component vaccines, however, were noted to require difficult purification processes and to have the disadvantage of usually being poor immunogens. Concern was also expressed that subsequent vaccine-induced immunity may not only fail to protect against natural virus challenge but, as in the case of inactivated measles vaccine, could conceivably cause a more severe clinical illness upon exposure to the natural virus.

The 1977 publication concluded that, while vaccination was one possible method for attaining the goal of prophylaxis, as of that date the efforts aimed at development of a HSV vaccine that was clinically acceptable and of proven efficacy were completely unsuccessful.

Since the time of the above-noted publication, the oncogenicity of Herpes simplex virus DNA and RNA has been the subject of confirmation by a number of investigators. See, e.g., Rapp, "Transformation by the Herpes Simplex Viruses", pp. 221-227 in "The Human Herpesviruses, An Interdisciplinary Perspective", Nahmias, et al., eds., Elsevier North Holland, Inc., New York, N.Y. (1981) and the publications cited therein. Such studies have essentially eliminated any remaining prospect for widespread use of live virus vaccines as well as those vaccine compositions including assertedly non-pathogenic, attenuated HSV strains as illustrated in U.S. Pat. No. 3,897,549.

Consistent with the general recognition of the desirability of vaccine compositions which exclude Herpes simplex virus DNA and RNA, the number of proposals for so-called "sub-unit" vaccines has increased. See, generally, Moreschi, et al., "Prevention of Herpes Simplex Virus Infections", pp. 440-445 in "The Human Herpesvirus, An Interdisciplinary Perspective", Nahmias, et al., eds., Elsevier North Holland, Inc., New York, N.Y. (1981). As one example, U.S. Pat. No. 4,158,054 proposes, but does not exemplify, a Herpes simplex sub-unit vaccine prepared by introducing inactivated whole virus particles into continuous loading zonal ultracentrifugation provided with a density gradient containing a haemolytic surfactant followed by binding of "split" sub-units isopycnically. As other examples, there may be noted the nucleic acid freed vaccines described by: Cappel, *Archives of Virology*, 52, pp. 29-35 (1976); Kitces, et al., *Infection and Immunity*, 16, pp. 955-960 (1977); Slichtova, et al., *Archives of Virology*, 66, pp. 207-214 (1980); and Skinner, et al., *Med. Microbiol. Immunol.*, 169, pp. 39-51 (1980). All the vaccine compositions of the foregoing publications were prepared by separative methodologies wherein greater or lesser care was taken to limit or eliminate nucleic acids from the fractions extracted. None of the vaccines, however, has been found to provide uniform protection of all vaccinate test animals from death by lethal challenge with Herpes simplex virus, a generally recognized requisite for continued evaluation.

Another Herpes simplex vaccine recently proposed and relatively thoroughly tested is a composition prepared by using what is asserted to be a viral glycoprotein sub-unit fraction. In Hilleman, et al., "Sub-unit Herpes Simplex Virus-2 Vaccine" pp. 503-506 in "The Human Herpesviruses, An Interdisciplinary Perspective" Nahmias, et al., eds., Elsevier North Holland, Inc., New York, N.Y. (1981), there is proposed a mixed glycoprotein sub-unit vaccine prepared using chick embryo fibroblasts infected with type 2 Herpes simplex virus. Briefly put, the vaccine antigen is prepared through glycoprotein release by treatment of infected cells with Triton X-100, digestion with DNase, purification on a lectin affinity column, and chromatography on Sephadex. The material is then treated with formalin and formulated in alum adjuvant. Vaccinated mice are noted to be protected against lethal challenge with Herpes simplex virus type 2 to a significantly greater degree than the alum adjuvant-treated controls. The glycoprotein was less effective in reducing mortality, however, than an aqueous, UV-inactivated whole virus vaccine (which itself did not prevent death in all vaccinated animals). The ability of the glycoprotein vaccine to induce formation of both homologous and heterologous type antibodies in humans was acknowledged to be limited, and cell mediated immunity assays with respect to homologous and heterologous types indicated both limited and transitory effects.

Of significant interest to the background of the present invention is the extensive body of information developed over the years concerning the major envelope glycoproteins of HSV. An extensive and extremely well-annotated monograph on this topic is presented in Norrild, "Immunochemistry of Herpes Simplex Virus Glycoproteins," in *Current Topics in Microbiology and Immunology* 90: pp. 67-106, Springer Verlag, Berlin (1980). The major topics of discussion are: the structure, synthesis and function of HSV-specified glycoproteins; the immunological reactivity of viral membrane proteins and their components; and demonstrations of the antigenic specificities of antibodies to individual glycoproteins.

Briefly summarized, the publication notes that Herpes simplex virus type 1 (HSV-1) and type 2 (HSV-2) specify at least five major glycoproteins, designated gA, gB, gC, gD and gE, which are to be found not only in the envelope of virus particles, but in the plasma membrane of infected cells and in detergent-treated cytoplasmic extracts derived from infected cells. These glycoproteins carry strong antigen determinants that include production of antibodies in an infected host organism, and they appear to be the major immunochemical stimuli at both humoral and cellular levels in the host. Some of the viral antigen determinants are in common (i.e., gB and gD), while some are specific for one or the other of the two virus types (i.e., gC and gE). [See also, Spear, "Herpes Viruses," pp. 709-750 in "Cell Membranes and Viral Envelopes, Vol. 2," Blough, et al., eds., Academic Press, New York, N.Y. (1980)]

Of even greater significance to the background of the present invention are the publications of one or both of the co-inventors and their co-workers which have, commencing in 1972, provided a most substantial portion of all available information concerning one of the HSV envelope glycoproteins, gD. Incorporated herein by reference, therefore, are the following:

(1) Cohen, et al., *J. Virol.*, 10: pp. 1021-1030 (1972);
(2) Ponce de Leon, et al., *J. Virol.*, 12: pp. 766-774 (1973);
(3) Cohen, et al., *J. Virol.*, 14: pp. 20-25 (1974);
(4) Cohen, et al., *J. Virol.*, 27: pp. 172-181 (1978);
(5) Eisenberg, et al., *J. Virol.*, 31: pp. 608-620 (1979);
(6) Eisenberg, et al., *J. Virol.*, 35: pp. 428-435 (1980); and (7) Cohen, et al., *J. Virol.*, 36: pp. 429–439 (1980).

The studies reported in the above-noted publications of the co-inventors and their co-workers have focused on gD of HSV-1 ("gD-1") and, in particular, on the isolation, purification and characterization of this glycoprotein. Using an extensive series of chromatographic steps, native gD-1 (previously known as CP-1 antigen) was purified in quantities sufficient to develop a monoprecipitin (or polyclonal) anti-CP-1 serum which had high titers of type-common neutralizing activity. Using anti-CP-1 as an immunological probe, it was demonstrated that gD-1 and the gD of HSV-2 ("gD-2") are both processed from lower molecular weight precursors to higher molecular weight product forms in infected cells by addition of oligosaccharides. Significant structural similarities between gD-1 and gD-2 were established by tryptic peptide analysis. Moreover, gD-1 was shown to be structurally identical whether isolated from infected human (KB) or from hamster (BHK21) cells.

Of considerable interest were the above-noted reports of the ability of the chromatographically purified gD-1 to provoke, in vivo, the generation of serum neutralizing antibodies which were fully protective of cells in culture against both HSV-1 and HSV-2 infections, as well as the ability of gD-1 to "block" HSV-1 and HSV-2 virus infection neutralization by protective sera.

Finally, recent studies have described the preparation and properties of several monoclonal antibodies to HSV glycoprotein gD and other HSV glycoproteins. One report of such a study [Dix, et al., *Infection and Immunity*, 34: pp. 192–199 (1981)] notes that certain monoclonal antibodies to gD-1 and gC-1 were capable of use in conferring passive immunological protection against lethal challenge with HSV-1. Passive immunization with a monoclonal antibody to gD-1 (termed "HD-1") was also attributed with providing protection with a lethal challenge with HSV-2.

Along with the above-described need for vaccine preparations for use in prevention and treatment of Herpes simplex virus disease states, there additionally exists a need for rapid and specific diagnostic tests for Herpes virus diseases and, more specifically, for antigenic substances useful in fluorescence, immunoperoxidase labelling, radioimmune and enzyme-linked immunoabsorbant assays. Such assays are commonly employed, for example, in the detection of Herpes simplex virus antibodies in samples of body fluids such as spinal fluids taken from those patients suspected of having encephalitis of Herpes simplex virus origin. See, e.g., Sever, "The Need for Rapid and Specific Tests for Herpesviruses," pp. 379–380 in "The Human Herpesviruses, An Interdisciplinary Perspective," Nahmias, et al., eds., Elsevier North Holland, Inc., New York, N.Y. (1981).

Subsequent to the Feb. 18, 1982 filing of applicants' copending U.S. patent application Ser. No. 350,021, Watson, et al. carried out nucleic acid sequencing studies of a protein coding region of the HSV-1 (Patton strain) genome corresponding to gD-1. The results of this work appear in *Science*, 218, pp. 381–384 (1982). Based on the nucleic acid sequence ascertained in these studies, Watson, et al. provided a putative 394-amino acid sequence for gD-1, indicating likely glycosylation sites, designating the first twenty amino acids at the amino terminal as a putative "signal" peptide, and noting the likelihood that a series of 25 amino acids at the carboxy terminal was involved in anchoring the glycoprotein to other membrane components. DNA vectors, neither of which included the first fifty-two codons (156 bases) of the published DNA sequence, were constructed for use in microbial expression of a "gD-related" polypeptide and a $\beta$-galactosidase/gD-1-related fusion polypeptide. Watson, et al. further reported that rabbits injected with the fusion protein product of *E. coli* expression of the fusion gene produced neutralizing antibodies to both HSV-1 and HSV-2. The directly-expressed polypeptide was not tested in vivo but was screened by immunoprecipitation assay against certain of the seventeen monoclonal antibodies screened for neutralization and RIP activity by the applicants and their co-workers in Eisenberg, et al., *J. Virol.*, 41, pp. 478–488 (1982). The directly-expressed gD-related polypeptide was noted to be immunoprecipitable by monoclonal antibodies of Groups I, IV and V (type common 4S, type 1 specific 1S, and RIP type 1 specific 55S and 57S) as well as polyclonal anti-HSV-1 rabbit antiserum. The polypeptide was reportedly not immunoprecipitated by monoclonals of Groups II and III (RIP type-common 12S and type-common 11S) or the group-undesignated monoclonal antibody 50S.

BRIEF SUMMARY

The present invention provides, for the first time, an immunologically active preparation of HSV-2 envelope glycoprotein, gD-2. This glycoprotein preparation of the invention is characterized, inter alia, by its freedom from association with other HSV envelope glycoproteins, by its freedom from association with viral or cellular DNA and RNA, and by its unique immunological properties. While chromatographic procedures may be employed, the preferred procedure for isolation of gD-2 is by means of selective reversible binding to a monoclonal anti-gD antibody-containing immunoadsorbent. A preferred source of gD-2 of the invention is a cytoplasmic extract of cells infected with an HSV-2 virus. Provided also are vaccine compositions including effective amounts of gD-2 and an immunologically acceptable diluent, adjuvant or carrier, as well as vaccination procedures involving administering such vaccine compositions to animals, including humans, for generating immunological responses protective against both HSV-1 and HSV-2 viral infection disease states. In one of its aspects, therefore, the invention provides a significant improvement in prior vaccination procedures involving administration of one or more component fractions of HSV particles for the purpose of generating a protective immunological response in a recipient animal against an HSV viral infection disease state. An antigenic mass of gD-2 is provided (in solution with an acceptable diluent, adjuvant or carrier) which is sufficient to generate an HSV-1 or HSV-2 protective response which includes formation in the host of antibodies corresponding to gD-2.

The present invention further provides, for the first time, an immunologically active preparation of HSV-1 envelope glycoprotein, gD-1, which is distinguished from prior art preparations by isolation by selective reversible binding to a monoclonal anti-gD antibody immunoadsorbent. This glycoprotein preparation is characterized, inter alia, by immunological properties superior to those of the most highly purified preparations of glycoprotein gD-1 heretofore available in the art and shares with the abovenoted gD-2 preparation freedom from association with other HSV envelope glycoproteins and viral or cellular DNA. A preferred source of gD-1 of the invention is a cytoplasmic extract of cells infected with HSV-1 virus. Provided also are vaccine compositions and vaccination methods of the highly protective character and type above described with respect to gD-2 of the invention. It is similarly an aspect of the invention that significant improvements are provided in prior methods for generating protective immunological responses against HSV viral infection diseases. As with gD-2 of the invention, a novel antigenic mass of gD-1 of considerable immunological significance is provided by the invention.

Vaccine compositions may include either gD-2 or gD-1 of the invention as above-characterized, or both, and are preferably administered in quantities providing unit doses of from 0.01 to 10.0 micrograms of immunologically active glycoprotein per kilogram of the recipient animal's body weight. Total protective doses may range from 0.1 to about 100 micrograms of antigen. Vaccine compositions may include, in addition to gD-1 and/or gD-2, immunologically acceptable diluents and carriers as well as commonly employed adjuvants such as Freund's Complete Adjuvant, saponin, alum, and the like.

A currently preferred monoclonal anti-gD antibody for use in obtaining gD-1 and gD-2 preparations of the invention is a purified IgG fraction derived from ascites fluids developed with the hybridoma line generating monoclonal antibody HD-1 described by Dix, et al., supra. See also, Periera, et al., *J. Virol.*, 29, pp. 724–732 (1980). Numerous other monoclonal anti-gD antibody preparations may also be employed with good results in the preparation of an immunoadsorbent for purification of gD-1 and gD-2 according to the invention.

Also provided by the invention are novel diagnostic reagents comprising gD-1 or gD-2 (or active fragments or replicas thereof) and immunologically active carrier or marker substances.

According to another aspect of the invention, immunologically active Herpes simplex virus glycoprotein D fragment replicas are provided which are suitably employed as immunoreactive materials in the manner herein described for use of the glycoproteins derived from viral sources. More specifically, the present invention provides polypeptides having amino acid sequences which duplicate in whole or part amino acid sequences extant in gD-1 and/or gD-2. Polypeptides of the invention preferably include the sequence:

RNH-Met-Ala-Asp-Pro-Asn-Arg-COOR' wherein R is hydrogen or one or more amino acids and R' is hydroxyl or one or more amino acids. As one example, the chemically synthesized sequence, NH$_2$-Ser-Leu-Lys-Met-Ala-Asp-Pro-Asn-Arg-Phe-Arg-Gly-Lys-Asp-Leu-Pro-COOR' (wherein R' is cysteine) has an established substantial homology to a nonglycosylated sequence of amino acids extant in the amino terminal region of both gD-1 and gD-2. This polypeptide includes the hydrophilic sequence, Met-Ala-Asp-Pro-Asn-Arg specified above and is immunoreactive with a Group VII monoclonal antibody (neutralization and RIP type common 170). The polypeptide alone and a species which has been "mounted" on a suitable carrier protein (keyhole limpet hemocyanin, KLH) by covalent linkage through the carboxy terminal cysteine residue have been employed in the manner of the aforementioned gD-1 and gD-2 isolates to immunize experimental animals prior to lethal challenge.

Other aspects and advantages of the present invention will become apparent to those skilled in the art upon consideration of the following detailed description of illustrative embodiments thereof.

DETAILED DESCRIPTION

HSV-1 glycoprotein gD-1 of the invention is obtained, and HSV-2 glycoprotein gD-2 is preferably obtained, by the rapid, high yield process of purification of HSV envelope glycoprotein mixtures on a monoclonal anti-gD antibody immunoadsorbent. As previously noted, suitable sources of HSV envelope glycoproteins include the envelope of virus particles, plasma membranes of infected cells and detergent-treated cytoplasmic extracts of HSV infected cells. The last-mentioned is a preferred source. Any number of monoclonal antibody-producing hybridoma cell lines may be used as anti-gD antibody sources in developing immunoadsorbent; and for purification of gD-1 and gD-2 of the invention. Among the antibody producing lines which may be employed are the seventeen hybridomas described in Eisenberg, et al., *J. Virol.* 41, pp. 478–488 (1982). The currently preferred monoclonal cell line is HD-1 described in Dix, et al., supra. The preferred monoclonal antibody HD-1 used for purification of both gD-1 and gD-2 by immunoadsorbent-affinity chromatography had the following properties: (1) as indicated in Dix, et al., supra, it neutralized the infectivity of both HSV-1 and HSV-2 to high titers and at approximately the same levels; (2) radioimmunoprecipitation (RIP) studies showed that greater than 90% of gD remained bound to HD-1 after 2 hours of incubation at 37° C.; and (3) HD-1 recognized gD in all strains of HSV-1 and HSV-2 tested. The conclusion obtained from analysis of these properties was that HD-1 recognizes a type-common antigenic determinant present on gD-1 and gD-2 and binds with a relatively high affinity. The preferred source of HD-1 antibodies is the IgG fraction of ascites fluid developed by intraperitoneal administration of HD-1 hybridoma cells to a suitable immunologically responsive animal. A preferred matrix is Sepharose 4B (Pharmacia) but other antibody immobilizing systems can be employed [See, e.g., *Biotechnology Newswatch*, Vol. 2, No. 2, page 3, (Jan. 18, 1982)].

Example 1, below, therefore illustrates the preparation of cytoplasmic extracts and the preparation (and characteristics) of HD-1 anti-gD antibody and HD-1 immunoadsorbent. Where particular conditions or procedures are designated as "previously" reported or disclosed, they are set out in one or more of the publications of the co-inventors and their co-workers listed supra.

EXAMPLE 1

1. Labeling of the Cells and Preparation of Cytoplasmic Extracts

Conditions for pulse labeling of infected cells have been previously reported. For purification of gD certain modifications were made to increase the amount of label incorporated and the amount of gD synthesized. For each experiment, ten roller bottles (490 cm$^2$) of confluent KB or BHK cells were infected with 20 p.f.u. HSV-1 (strain HF) or 10 p.f.u. HSV-2 (SAVAGE strain). At 2 hours post infection (pi) the cells were overlaid with 50 ml of Eagle's Minimal Essential Medium (MEM) containing 5% Natal Calf serum (Dutchland Co.). At 5 hours pi the medium was decanted from one of the roller bottles and the cells were washed with warmed (37° C.) Hank's salts and overlaid with 5.0 ml of Hank's salts containing the appropriate radioisotope: [$^{35}$S]-methionine (specific activity, >600 Ci/mmol) 1 mCi; [2,3-$^3$H]-arginine (specific activity 15 Ci/mmol); 1 mCi. After 30 minutes the cells were overlaid with 25 ml of prewarmed complete MEM and all of the bottles were incubated for an additional 7 hours. At 12 hours pi, labeled and unlabeled cells were washed 4 times with iced saline containing 0.1 mM phenyl-methyl-sulfonyl fluoride (PMSF) and cytoplasmic extracts were prepared. To each roller bottle of cells, 5 ml of cold lysing buffer (0.01M Tris buffer, pH 7.5, containing 0.15M NaCl, 0.5% Nonidet P-40 (NP-40), 0.5% sodium deoxycholate) were added and the cells were incubated for approximately 5 minutes at 4° C. Tolyl-sulfonyl phenylalanyl-chloromethyl ketone (TPCK) and N-ɑto-syl-L-lysine chloromethyl ketone (TLCK) were added, each at a concentration of 0.1 mM to inhibit proteolytic activity. The lysed cells were scraped from the bottles and centrifuged at 1200 rpm for 10 minutes to remove nuclei. The cytoplasm was centrifuged at 100,000×g for 1 hour. The cytoplasmic extracts were stored at −70° C.

2. Purification of IgG from HD-1 Ascites Fluid

Purification of IgG was performed essentially as described by Montgomery, et al., *Biochemistry*, 8: pp. 1247-1258 (1969). Briefly, saturated ammonium sulfate (7 ml) pH 7.0 was added slowly to HD-1 ascites fluid (7 ml) in an ice bath, stirred for 2 hours and centrifuged for 30 minutes at 15,000×g. The precipitate was resuspended in 10 ml of 0.01M phosphate buffer, pH 7.3 (PB) and dialyzed extensively against PB. Further fractionation of immunoglobulin was performed on Whatman DE-52. Sixty-five mg of IgG were obtained from 7 ml of ascites fluid. SDS-PAGE analysis of the purified IgG showed only two Coomassie blue stained bands corresponding to the heavy and light chain of the IgG 2A molecule.

3. Preparation of the HD-1 Immunoadsorbent

Two grams of cyanogen bromide-activated Sepharose 4B (Pharmacia) were prepared as follows: The gel was swollen at room temperature for 1 hour in 0.001N HCl, washed by filtration with 400 ml of 0.001N HCl and resuspended in 5 ml of 0.2M sodium carbonate buffer at pH 8.5 containing 1M NaCl. Twenty mg of IgG in 5 ml of PB were added to the gel suspension. The mixture was stirred for two hours at room temperature, filtered and then resuspended in 10 ml of 1M ethanolamine, pH 8.0. The mixture was stirred for an additional 2 hours, washed successively by filtration with 0.1M sodium acetate, pH 4.0 containing 1M NaCl and then with 0.1M sodium borate pH 8.0, containing 1M NaCl. The mixture was equilibrated at 4° C. with washing buffer (0.01M Tris, pH 7.5, 0.1% NP-40, 0.5M NaCl and 0.1 mM PMSF). The efficiency of IgG coupling to the activated-Sepharose was greater than 97%.

The following Example illustrates purification of gD-1 and gD-2 according to the present invention along with characteristics of purity of the preparations obtained.

EXAMPLE 2

All procedures were carried out at 4° C. In a typical experiment, the starting material consisted of 55 ml of unlabeled cytoplasmic extract plus 5 ml of radioactively labeled cytoplasmic extract (100-180 mg protein). The extract was centrifuged at 100,000×g for 1 hour, added to the immunoadsorbent and recycled through the column five times. Sixty ml were collected. This fraction was termed the flow through (FT). The column was washed overnight with washing buffer and gD was eluted with 200 ml of 3M KSCN, pH 7.8. The KSCN fraction was concentrated approximately 100 fold using an Amicon PM-30 membrane for gD-1 and a PM-10 membrane for gD-2. The concentrated sample was dialyzed extensively against a modified lysing (ML) buffer (0.01M Tris pH 7.5, 0.1% NP-40, 0.15M NaCL, 0.1 mM PMSF). Samples of purified gD were stored at −70° C. The same purification procedures were applied to labeled uninfected cells. Analysis by SDS-PAGE established that host proteins were not bound on the immunoadsorbent column to any appreciable extent.

Molecular weights for gD-1 and gD-2 corresponded well to those previously reported. Tryptic peptide analysis of purified gD-1 and gD-2 was performed according to procedures previously reported and the profiles obtained also provided evidence of high degrees of purification of the glycoproteins.

A quantitative radioimmunoprecipitating assay (RIP) was employed to screen cytoplasmic, FT and KSCN fractions for gD activity. This procedure involved a simple antibody binding assay. Increasing amounts of HD-1 IgG were added to a fixed amount of radioactively labeled purified gD-1 or gD-2. The mixtures were incubated for 20 minutes at 37° C. and *S. aureus* was added to collect the immune complexes. The complex was washed and suspended in SDS-disrupting buffer. Duplicate aliquots of each sample were counted in a scintillation counter and the rest of the sample was analyzed by SDS-PAGE to be certain that all of the radioactivity bound by HD-1 was associated with gD. To express the results in terms of ng gD bound, the amount of protein in the KSCN fraction was first determined. The method of Lowry, et al., *J. Biol. Chem.*, 193: pp. 265-275, as modified by Dulley, et al., *Analyt. Biochem.*, 64: pp. 136-141 (1975), was employed for determining protein concentration in the presence of detergent. The proportion of labeled gD in the original sample that was trichloracetic acid (TCA) precipitable was then determined. The amount of purified gD bound to HD-1 IgG was then determined according to the following equation:

$$\text{ng purified gD bound} = \frac{\text{CPM gD bound to antibody}}{\text{TCA precipitable CPM of gD}} \times \text{total ng purified gD}$$

The results obtained indicated that the amount of gD-1 or gD-2 bound to HD-1 IgG was directly proportional to the concentration of both antigen and antibody. The assay was linear over a range of 25-200 ng of gD-1 or gD-2 and 0.1-1.0 μg HD-1 IgG. The maximal binding of labeled antigen to excess antibody was approximately 48% for gD-1 (6 experiments) and approximately 53% for gD-2 (4 experiments). When the unbound gD-1 and gD-2 were analyzed by SDS-PAGE, the proteins had the same electrophoretic mobility as the bound glycoproteins. Addition of more *S. aureus* did not increase the amount of gD bound. However, when anti-CP-1 serum (prepared as previously described) was added to unbound gD-1, an additional 7-10% of the glycoprotein was immunoprecipitated. These results suggest that the determinant recognized by HD-1 may have been partially inactivated during purification of gD-1 and gD-2.

Using the slopes of the lines in the linear portion of the quantitative RIP assay results, a unit of HD-1 binding for gD-1 and gD-2 was defined as: ng glycoprotein per µg of HD-1. Using this definition, the amount of gD activity in each fraction of the purification procedure was determined by the quantitative RIP assay. The results obtained are set out in Table 1 below and showed that the procedure resulted in a 421 fold increase in gD-1 activity and a 198 fold increase in gD-2 activity. The recovery of gD-1 (35% of the starting activity) was higher than that of gD-2 (16%). The data in Table 1 emphasize the high yields (150 µg gD-1 and 82 µg gD-2) and specific activity of both glycoproteins.

TABLE 1

Purification of gD-1 and gD-2 of HSV by Immunoadsorbent Chromatography

| FRACTION | Cytoplasm | | Flow Through | | KSCN | |
|---|---|---|---|---|---|---|
| Parameter Measured | gD-1 | gD-2 | gD-1 | gD-2 | gD-1 | gD-2 |
| Total Protein (mg)[a] | 180 | 100 | 176 | 99 | 0.150 | 0.082 |
| Total Units of gD[b] | 1714 | 1364 | 127 | 129 | 600 | 222 |
| Specific Activity of gD[c] | 9.5 | 13.6 | 0.72 | 1.3 | 4000 | 2700 |
| Increase in Specific Activity | 1 | 1 | 0.075 | 1.3 | 421 | 198 |
| Total Amount of Active gD (mg)[d] | 0.205 | 0.270 | 0.015 | 0.025 | 0.072 | 0.044 |
| Recovery of gD Activity (%) | 100 | 100 | 7.4 | 7.5 | 35 | 16 |

[a]Determined by modified method of Lowry, et al., supra.
[b]A unit is defined as: $\frac{\text{ng gD bound}}{\text{µg HD-1 IgG}}$.
For gD-1, 1 unit = 120 ng; for gD-2, 1 unit = 198 ng.
[c]Units/mg protein.
[d]Determined from data obtained for KSCN fraction to be 48% of the total protein for gD-1 and 53% of the total protein for gD-2. In the case of the cytoplasmic and FT fractions, it was assumed that gD-1 and gD-2 were 100% active.

An amino acid analysis was conducted on samples of purified gD-1 and gD-2. Samples of gD-1 and gD-2 were dialyzed extensively against water and were brought to 6M HCl and heated in vacuo at 110° C. for 24, 48 and 72 hours. Amino acids were quantitated on a Dionex D500 Amino Acid Analyzer. The values for serine and threonine were calculated by extrapolation to zero time. The amounts of isoleucine, leucine and valine were calculated on the basis of 48- and 72-hour hydrolyses. Cysteine was determined after performic acid oxidation. Analytical results, set out in Table 2, indicate that the overall composition of the two purified glycoproteins is similar but not identical, a finding which agrees with predictions based on previously described tryptic peptide analysis.

TABLE 2

| | Amino Acid Composition | |
|---|---|---|
| | Residues/molecule[a] | |
| Amino Acid | gD-1 | gD-2 |
| Asp | 40 | 35 |
| Thr[b] | 24 | 23 |
| Ser[b] | 46 | 62 |
| Glu | 53 | 59 |
| Pro | 35 | 27 |
| Gly | 47 | 51 |
| Ala | 37 | 44 |

TABLE 2-continued

| | Amino Acid Composition | |
|---|---|---|
| | Residues/molecule[a] | |
| Amino Acid | gD-1 | gD-2 |
| Val[c] | 23 | 20 |
| Met | 5 | 6 |
| Ile[c] | 23 | 19 |
| Leu[c] | 38 | 32 |
| Tyr | 15 | 7 |
| Phe | 11 | 5 |
| His | 8 | 11 |
| Lys | 16 | 22 |
| Arg | 22 | 16 |
| Cys | 12 | 11 |
| Trp | ND[d] | ND |

[a]For gD-1, the total number of amino acids was assumed to be 455 (average molecular weight 110). For gD-2, the total number of amino acids was assumed to be 450 (average molecular weight 110). The molecular weight of gD-1 minus carbohydrate was assumed to be 50,000. The molecular weight of gD-2 minus carbohydrate was assumed to be 49,500.
[b]The values were extrapolated to zero time.
[c]Based on the average value of 48 and 72 hour hydrolyses.
[d]Not determined.

The following Example illustrates the immunological activity of purified gD-1 and gD-2 of Example 2.

EXAMPLE 3

Two procedures were employed to ascertain the biological activity of gD-1 and gD-2 prepared according to Example 2. The first procedure involved determination of HSV neutralizing activity of antisera produced in response to immunization with gD-1 and gD-2. The second procedure assayed the ability of purified gD-1 and gD-2 to block serum neutralization capacity of anti-CP-1 serum prepared as previously described. It is noteworthy that this is believed to be the first determination of such immunological activities for gD-2 ever conducted.

In the first procedure, anti-gD-1 and anti-gD-2 sera were prepared as follows. CAF1 mice (10 weeks old, female) were immunized with immunoadsorbent purified gD-1 and gD-2. Each mouse received a series of four IP injections of the appropriate antigen (total immunizing dose of 7.5 µg of protein) emulsified in complete Freund's adjuvant. The following schedule was used: The first injection was 3 µg. This was followed by injections of 1.5 µg of gD at days 7, 21, and 35. After 45 days, the mice were bled.

Neutralization titers were determined by a modification of the plaque reduction technique previously described. Briefly, various dilutions of antiserum were each incubated for 90 minutes at 37° C. with 60 p.f.u. of virus in a final volume of 40 µl. One half of each mixture (30 p.f.u. of virus) was added to one well of a 96 well plate (Costar) of BHK cells. After a 1 hour adsorption period, the cells were overlaid with fresh medium, incubated for 24 hours at 37° C. and the plaques counted under an inverted microscope. The reciprocal of the greatest dilution of serum causing a 50% reduction in titer compared with pre-immune serum was selected as the neutralizing titer.

All of the mice produced a monoprecipitin antiserum which immunoprecipitated precusor pgD in a type-common fashion. This observation is further evidence of the purity of gD-1 and gD-2. Table 3 shows that gD-1 and gD-2 stimulated the production of high titers of type-common neutralizing antiserum in each immunized mouse. The overall conclusion from these experiments is that both gD-1 and gD-2 were purified in a biologically active form.

TABLE 3

| Antiserum Designation | Prepared Against Mouse Number | Neutralization Titer[a] | |
|---|---|---|---|
| | | HSV-1 | HSV-2 |
| anti-gD-1 | 1 | 2048 | 1536 |
| | 2 | 1536 | 512 |
| | 3 | 1536 | 512 |
| anti-gD-2 | 1 | 192 | 512 |
| | 2 | 512 | 1024 |
| | 3 | 1024 | 1024 |
| | 4 | 1024 | 1536 |
| | 5 | 192 | 512 |

[a]Results are expressed as the reciprocal of the greatest dilution of serum resulting in a 50% reduction of p.f.u. as compared with appropriate virus and pre-immune mouse serum controls (22). Anti-CP-1 serum (rabbit) had a neutralization titer of 512 against HSV-1 and 256 against HSV-2 when tested in the same assay system.

Preparation of samples for the second, serum blocking assay was as follows. An aliquot of purified gD-1 or gD-2 (30–50 μg protein) in ML buffer was dialyzed successively against decreasing concentrations of NP-40 (0.1%, 0.01%, 0.001%, no NP-40) contained in Tris buffer, 0.01M, pH 7.5, 0.15M NaCL. After each dialysis step, a portion was removed and analyzed for radioactivity and binding activity by the quantitative radio-immunoprecipitation assay. The only significant loss occurred at the last step of dialysis (no NP-40). At that step, approximately 50% of the trichloroacetic acid precipitable radioactivity was lost, but of the remaining 50%, there was no significant loss in HD-1 binding activity.

The assay was performed in 96 well plates by a modification of the method previously described. Briefly, dilutions of gD-1 or gD-2 were mixed with a fixed dilution of antiserum. The dilution of antiserum chosen was that dilution which would cause a 75–90% neutralization of 60 p.f.u. of virus. The antigen-antibody mixture was incubated for 1 hour at 37° C. and then each mixture was added to 60 p.f.u. of virus (in a final volume of 40 μl). The mixtures were incubated for 90 minutes at 37° C. and one half of each mixture was added to one well of a 96-well plate (Costar) of BHK cells. After a 1 hour adsorption period, the cells were overlaid with fresh medium, incubated for 24 hours at 37° C. and the plaques counted under an inverted microscope. The 50% endpoint was that dilution of gD which blocked the neutralizing capacity of the serum by 50%.

It had previously been shown that the purified CP-1 antigen stimulates the production of high titers of type-common virus neutralizing antibody. If purified gD-1 and gD-2 possess the same biological activity, they should be capable of combining with anti-CP-1 serum (as well as any serum containing neutralizing antibody directed to gD) and blocking its neutralizing capacity. Preliminary experiments showed that the levels of NP-40 present in the glycoprotein fractions were inhibitory to both virus and cells. Dialysis of the glycoproteins against Tris buffer containing saline but no NP-40 did not significantly alter their binding activity and the preparations were no longer inhibitory. However, this procedure resulted in a loss of approximately 50% of the protein. Each preparation of gD was titered for serum blocking capacity against anti-CP-1 serum and the results of one experiment (corrected for the loss of protein) are shown in Table 4. It can be seen that both glycoproteins had approximately the same serum blocking capacity. This experiment clearly showed that gD-2 was able to block neutralization of a heterologous antiserum.

TABLE 4

| | Concentration of gD Required[a] | |
|---|---|---|
| Virus Employed | gD-1 | gD-2 |
| HSV-1 | 37 | ND[b] |
| HSV-2 | 35 | 30 |

[a]ng of gD required to block by 50% the capacity of anti-CP-1 serum to neutralize 30 p.f.u. of either HSV-1 or HSV-2
[b]Not determined The following Example illustrates effectiveness of gD-1 vaccine composition of the invention in protection of vaccinated animals against death by massive challenge with lethal strains of both HSV-1 and HSV-2.

EXAMPLE 4

The inoculant employed consisted of a solution of 1 microgram of gD-1, isolated according to Example 2 from cytoplasm of cells infected with HSV-1 strain HF, in Freund's Complete Adjuvant. Each Balb/c mouse in a first inoculated group received a total of five intraperitoneal injections over a period of two months. Seven days after the final inoculation, serum of blood taken from the retro-orbital plexis was assayed in the radioimmune precipitation (RIP) procedure of Eisenberg, et al., J. Virol., 31, pp. 608–620 (1979) and neutralizing antibody procedure of Cohen, et al., J. Virol., 19, pp. 1021–1030 (1972). All immunized animals tested positively, displaying neutralizing antibody titers of from about 1:16 to about 1:128 and immunoprecipitation results indicating production of antibodies only to gD. Because antibody immunoprecipitated both gD-1 and gD-2, it was apparent that all ten vaccinates had produced a type common neutralizing antibody to gD of HSV.

Fourteen days after the final inoculation, the first group of 10 vaccinated mice was assembled which displayed a range of serum neutralizing antibody titers (3 at ~1:128; 3 at ~1:64; and 4 at ~1:32). These 10 mice, along with 9 control (unvaccinated) mice were administered intraperitoneally a dose of $4 \times 10^6$ p.f.u. of Patton strain HSV-1 (approximately 4 times the $LD_{50}$ for this strain). All control animals died within seven days, while all vaccinates were long term survivors and never appeared unhealthy.

A second group of 8 vaccinated mice displaying a range of serum neutralizing antibody titers of 1:16 to 1:128 was assembled. Each received an additional 1 microgram dose of gD-1. These, together with 11 control mice were given an intraperitoneal challenge of $1 \times 10^6$ p.f.u. of (lethal) strain 186 HSV-2. Within 10 days, 8 of the 11 control animals had died. The remaining 3 controls survived and were later sacrificed. All vaccinated animals remained healthy and displayed no evidence of neurological disorders (e.g., extreme quiescence) associated with intraperitoneal HSV administration.

The following Example illustrates effectiveness of gD-1 vaccine compositions according to the present invention in stimulating formation of neutralizing antibodies.

EXAMPLE 5

Four rabbits were involved in this procedure. The two vaccinated animals received slightly varying intramuscular doses of gD-1 and gD-2 prepared according to Example 2 in a vaccine composition with Freund's Complete Adjuvant. The first, gD-1, vaccinate received a total of four doses, of 10, 10 and 5 and 5 micrograms, respectively, over a period of four weeks. The second animal received doses of 9, 9, 4.5 and 4.5 micrograms of gD-2 over the same period. Each animal received a "boost" of 1 microgram of gD-1 approximately ten days later and both animals were bled three days after the boost.

Serum neutralizing antibody determinations were run on the serum collected. The results obtained were approximately three to five times greater than those which were obtained using the chromatographically purified CP-1 preparation in Cohen, et al., *J. Virol.*, 27, pp. 172-181 (1978). CP-1 according to this reference was the most highly purified and active glycoprotein gD isolate known to the art prior to the present invention.

Although not substantiated by controlled experimental study, vaccines of the invention achieve effects beyond protection against disease states from post-vaccination infection of recipients in the form of limiting of ganglionic infection. Such results would be consistent with previous reports of lowered incidence of latent HSV-2 infection in animals challenged with HSV-2 after inoculation with live HSV-1. See, e.g., McKendall, *Infection and Immunity*, 16, pp. 717-719 (1977). Vaccines of the invention could also be expected to limit or eliminate persistent ganglionic infection which has already been established in the recipient prior to vaccination. See, e.g., Hilleman, et al., supra, and Moreschi, et al., supra.

While the foregoing detailed description of the invention deals with the use of Herpes simplex virus glycoproteins gD-1 and gD-2 isolated from "natural" sources, it will be understood by those skilled in the art that the present invention comprehends glycoprotein replicas, fragments of glycoproteins or fragments of glycoprotein replicas which also display the in vitro and in vivo antigenic character of the "whole" glycoprotein compounds. It is likely, for example, that effective vaccine compositions may be prepared using non-glycosylated or partially glycosylated polypeptides which themselves may be prepared by recombinant methods (see, e.g., Cohen, et al., U.S. Pat. No. 4,237,224) or even by entirely synthetic methods. [See, e.g., Zuckerman, "Developing Synthetic Vaccines", *Nature*, 295, No. 5845, pp. 98-99 (1982) and Dreesman, et al., "Antibody to Hepatitis B Surface Antigen After a Single Inoculation of Uncoupled Synthetic HBsAg Peptides", *Nature*, 295, No. 5845, pp. 158-160 (1982)].

In the recent past there have been many similar reports of immunological activity for synthetic polypeptides which are replicas of (i.e., substantially duplicate amino acid sequences extant in) naturally-occurring proteins, glycoproteins and nucleoproteins. More specifically, relatively low molecular weight polypeptides have been shown to participate in immune reactions which are similar in duration and extent to the immune reactions of physiologically significant proteins such as viral antigens, polypeptide hormones and the like. Included among the immune reactions of such polypeptides is the provocation of the formation of specific antibodies in immunologically active animals. See, e.g., Lerner, et al., *Cell*, 23, 309-310 (1981); Ross, et al., *Nature*, 294, 654-656 (1981); Walter, et al., *P.N.A.S. (USA)*, 77, 5197-5200 (1980); Lerner, et al., *P.N.A.S. (USA)* 78, 3403-3407 (1981); Walter, et al., *P.N.A.S.-(USA)*, 78, 4882-4886 (1981); Wong, et al., *P.N.A.S.-(USA)*, 78, 7412-7416 (1981); Green, et al., *Cell*, 28, 477-487 (1982); Nigg, et al., *P.N.A.S.(USA)*, 79, 5322-5326 (1982); and Baron, et al., *Cell*, 28, 395-404 (1982). See, particularly Lerner, "Synthetic Vaccines" *Scientific American*, 248, No. 2, 66-74 (1983).

Consistent with the above-noted disclosures of advantageous immunological activity for gD-1 and gD-2 isolates, non-glycosylated polypeptides of the invention have been prepared which share immunological characteristics of the whole glycoproteins despite the fact they comprise replicas of only minor portions of the active isolates.

In the preparation of immunologically active polypeptides according to the invention, it was initially noted that the most desirable characteristics for an anti-Herpes synthetic peptide vaccine constituent would be the following: (1) it would comprise a relatively small sequence of amino acids; (2) the sequence would be a replica of a sequence common to gD-1 and gD-2; and (3) the sequence would comprise an entire, continuous antigenic determinant (epitope) rather than a portion of a conformational determinant.

If one accepts the putative amino acid sequence provided by Watson, et al., the gD-1 glycoprotein consists of 394 amino acids (or 374 if the putative "signal" sequence is deleted) and a 342 amino acid sequence which was microbially expressed is capable of raising neutralizing antibodies to both HSV types I and II. A review of the Watson et al. sequence provides no clear indication of where in the microbially expressed sequence there exist smaller amino acid sequences which might constitute epitopes with respect to which protective hormonal and cellular response might be generated. Analysis of the sequence according to the method of Hopp, et al., *P.N.A.S.(USA)*, 78, 3824 (1981) shows a number of small amino acid sequences which are hydrophilic and hence potentially antigenic. Analysis of the sequence by the method of Chou, et al, *Ann.Rev.Biochem.*, 47, 251 (1978) shows a number of potential bends in secondary structure of gD-1 glycoprotein which may have antigenic significance. Neither of these analytical methods, however, provides any indication of whether a potentially antigenic sequence forms a single continuous determinant or merely comprises a part of a discontinuous determinant. Further, in the absence of amino acid sequence data for gD-2, no direct comparison for a potentially type-common determinant can be made.

Information helpful in determining the location of continuous antigenic determinants of gD-1 was provided by denaturization and in vitro synthesis studies by applicants. Briefly put, gD-1 isolated according to prior Examples 1 and 2 was denatured using SDS and mercaptoethanol with boiling water. The denatured gD-1 product retained its ability to protect immunized animals against HSV type II infection and also retained its immunoreactivity with polyclonal, serum-derived antibody preparations. The denatured material did not retain its reactivity with all the available monoclonal antibodies; only monoclonal antibodies of Groups V and VII were able to immunoprecipitate the denatured gD-1. This indicated that there existed at least two continuous (and not conformational) antigenic determinants within gD-1. This conclusion was further supported by in vitro synthetic work wherein messenger RNA specifying gD-1 was used to generated a 49K protein which was immunoreactive only with polyclonal antibodies and monoclonals of Groups V and VII. In vitro membrane processing of the 49K polypeptide to delete any signal region present and add saccharides yielded a 52K glycoprotein which also retained reactivity only with polyclonal antibodies and monclonals of Groups V and VII.

The additional fact that prior screening work [see Eisenberg, et al., *J. Virol.*, 41, pp. 478-488 (1982) and *J. Virol.*, 41, pp. 1099-1104 (1982)] had shown that the Group VII monoclonal antibodies were type-common made the epitope for this antibody (if it could be found) a good candidate for testing as a synthetic vaccine constituent. Work was therefore carried out to assist in the localization of the continuous sequence which formed the epitope for reactivity with the Group VII monoclonal antibody.

The development of information helpful in ascertaining the location of the epitope to the Group VII antibody included isolation of membrane bound fragments from trypsonized membrane preparations of the type used in the in vitro synthetic procedures noted above. The isolated fragments retained cross-reactivity with the polyclonal antibodies and with antibodies of Group VII, but not those of Group V. This indicated that the Group VII epitope was in the area of the amino terminal end of the glycoprotein rather than the carboxy terminal. Further information concerning the Group VII epitope location was provided through analysis of applicants' prior immunobinding studies which revealed that the Group VII antibody binds to a 12K fragment remaining after exhaustive V8 protease digestion of gD-1 and gD-2. That the 12K fragment was included within the 38K fragments brought down by the other monoclonals was verified by an overlap in the tryptic peptide patterns revealed by ion exchange chromatographic analysis of two fragments. (Collateral studies of the 38K fragments indicated that it included methionine residues in the early portion of the sequence.)

Among the tryptic peptides of the 12K fragments which had been found to be common to gD-1 and gD-2 was a fragment designated "F". This type common sequence was, by definition, one which included an arginine residue at the right-hand end at which trysine operated to separate it from other amino acid residues. Preliminary analysis of isolated "F" fragments indicated that it had molecular weight in the range of about 600 and that it included both a proline residue and a methionine residue. However, the precise location of the type common "F" fragment in the gD-1 and gD-2 glycoproteins could still not be dispositively made solely on the basis of the Watson, et al. putative gD-1 sequence and required verification of amino acids sequences by direct amino acid analysis performed on both gD-1 and gD-2 isolates.

The following example relates to amino acid sequencing studies carried out on gD-1 and gD-2.

EXAMPLE 6

1. Preparation of Virus and Cells

Conditions for the growth and maintenance of KB and BHK cells and the procedure used for the preparation of virus stocks of HSV-1 (strain HF) and HSV-2 (strain SAVAGE) and the plaque assay were as described previously. For infection, an input multiplicity of 20 PFU of HSV-1 or 10 PFU of HSV-2 per cell was employed.

2. Metabolic Labeling

For the methionine, lysine and arginine radioactive labels employed, a 75 cm$^2$ bottle of confluent KB or BHK cells was infected with HSV-1 or HSV-2. At 2h p.i., the cells were overlaid with Eagle's minimal medium containing 1/10 the normal concentration of methionine, arginine or lysine. Pulse-labeling was carried out at 6 hours p.i. by incubating infected cells for 15 min., in 4.5 ml Hank's salts containing one of the following isotopes: [$^{35}$S]-methionine, (specific activity 600 Ci/mmole, 1 mCi); [2,3-$^3$H]-arginine, specific activity, 15 Ci/mmole, 1 mCi; [4,5-$^3$H]-lysine, specific activity 60-80 Ci/mmole, 1 mCi. The monolayers were washed with iced saline, lysed, and cytoplasmic extracts prepared as described previously. For the leucine and alanine radioactive labels, infected cells were pulse-labeled at 6 hours p.i. for 15 minutes in Hank's salts, then overlaid with Eagles minimal medium and incubated at 37° C. for an additional 2 hours. The following radioisotopes were used: [4,5-$^3$H]-leucine, specific activity 50 Ci/mmole, 1 mCi; [3-$^3$H]-alanine, specific activity, 75 Ci/mmole, 500 µCi.

3. Iodination of Purified gD

To determine the positions of tyrosine residues, gD-1 and gD-2 were each purified by immunoadsorbant chromatography and 15 µg of each protein was iodinated by the chloramine T procedure of Greenwood, et al., *Biochem. J.*, 89, pp. 114-123 (1963).

4. Preparation of Samples for Amino Acid Sequencing

Each cytoplasmic extract was immunoprecipitated with anti-CP-1 serum (prepared in mice against purified gD-1). *Staphylococcus aureus* Cowan strain I (IgSorb, New England Enzyme Center) was employed to collect antigen-antibody complexes. The precipitates were washed and the antigen-antibody complexes were disrupted as described previously. A portion was analyzed by SDS-PAGE. Bovine serum albumin (100 µg) was added to the remainder and the protein was precipitated with 25% trichloracetic acid at 4° C. for 17 h. The precipitates were collected by centrifugation at 13,000×g for 30 min, dissolved in 1 ml of 0.1N NaOH, dialyzed exhaustively against distilled H$_2$O and lyophilized. A similar procedure was employed to immunoprecipitate iodinated gD-1 and gD-2.

5. SDS-PAGE

SDS-PAGE was carried out in slabs of 10% acrylamide cross-linked with 0.4% N,N'-diallyltartardiamide (DATD) by essentially the same method described by Spear, *J. Virol.*, 17, pp. 991-1008 (1976). After electrophoresis, the gels were stained with Coomassie brilliant blue, dried on filter paper, and exposed to Kodak XAR-5 film.

6. Amino Acid Sequence Analysis

Stepwise Edman degradation of radiolabeled gD-1 and gD-2 was accomplished in a Beckman 890 B protein sequencer. See, Edman, et al., *Eur.J.Bioch.*, 1, pp. 80-91 (1967) and Hermodson, et al. *Biochemistry*, 11, pp. 4493-4502 (1972). The lyophilized radiolabeled samples were dissolved in H$_2$O and mixed with 50 mmoles of sperm whale myoglobin. The samples taken at each step were dried, resuspended in 100 µl acetone, and transferred to scintillation vials. The tubes were washed with an additional 50 µl of acetone and 100 µl of ethyl acetate, the vials were dried over N$_2$ and analyzed by scintillation counting. The samples containing [$^{125}$I] were analyzed directly in a gamma counter. In each run, the positions of all labeled and several unlabeled steps were confirmed by high-pressure liquid chromatography of the myoglobin carrier protein-derived amino acids.

The general procedure used for labeling gD was to infect cells with either HSV-1 or HSV-2 then to metabolically label the cells with the particular radioactive amino acid. For methionine, arginine, and lysine a 15 min pulse carried out at 6 hrs. p.i. was sufficient to obtain enough radioactive label incorporated into gD for sequencing. Under these conditions of labeling, most of the radioactivity was found in the precursor forms of gD-1 (53,000 daltons) and gD-2 (52,000 daltons). For alanine incorporation into gD-1 and leucine incorporation into both gD-1 and gD-2, it was necessary to label for an additional 2 hours in order to get a sufficient amount of labeled gD. Under these conditions of labeling, both the precursor and product forms of the glycoproteins were labeled. At the end of the labeling period, cytoplasmic extracts were prepared and immunoprecipitated with a polyclonal antibody prepared against purified gD-1. In order to carry out sequencing studies of labeled tyrosine, gD-1 and gD-2 were purified from infected cell extracts by immunoabsorbant chromatography and the purified proteins were iodinated with [$^{125}$I] using the Chloramine T procedure.

SDS-PAGE analysis of the radiolabeled preparations used for automated N-terminal sequencing revealed that when metabolic labeling was employed, over 95% of the radioactive label was present in either the precursor or product (or both) forms of gD-1 and gD-2. In the case of iodinated gD-1, some label was present in lower molecular weight polypeptides. It was not clear whether these fragments of gD were generated as a result of iodination or were due to proteolytic digestion of purified gD-1 which occurred prior to iodination.

Profiles of automated Edman degradations of radiolabeled gD-1 and gD-2 were prepared and the sequences derived from these profiles are shown in Table 5 below wherein sequence numbers assigned by Watson, et al. for the predicted amino acid sequence are shown in parentheses.

at residues 3, 5 and 12. However, only gD-1 contained an alanine at position 7. Both proteins had methionine residues at position 11, but only gD-1 had a methionine residue at position 8. In the case of arginine, both proteins had arginine residues at positions 16 and 18 and only gD-2 appeared to have an arginine (rather than a lysine) at position 20. For leucine, there were radioactive peaks at residues 4, 9, 22, 25 and 28 of gD-1. For gD-2 there were [$^{3}$H]-leucine peaks at residues 4, 23 and 28 and possibly at residue 25. It should be noted that for both proteins, the leucine profiles exhibited a high background of radioactivity. This may have been due to the very long labeling time required to obtain sufficient incorporation of this particular amino acid label. However, the [$^{3}$H]-leucine peaks for gD-1 correlate precisely with the positions of leucine in the Watson, et al. deduced amino acid sequence.

Table 5 shows that the above-noted data for gD-1 can be aligned farily well with the deduced amino acid sequence of gD-1 beginning at residue 26 of the deduced sequence. One difference is at residue 8 (33 of the deduced sequence) where the above-noted data indicates that gD-1 strain HF) contains a methionine residue. However, gD-2 (strain SAVAGE) did not. The residue predicted by nucleic acid sequencing (using strain Patton of HSV-1) is a serine. The differences noted at this position might be due to strain and type variation. However, an alteration from a methionine to a serine would require at least two base changes.

The data indicates the first 25 amino acids of the Watson, et al, predicted sequence are not present in the protein as isolated from infected cells. This stretch of amino acids is largely hydrophobic, the only exceptions being an arginine at predicted residues 7 and 24 and a histidine at predicted residue 21. The above data would suggest that gD-1 does indeed possess a signal peptide and that it may be as long as 25 amino acids. Since both gD-1 and gD-2 were found to begin with a lysine residue, it would appear that gD-2 DNA will be found to contain region coding for a signal peptide.

TABLE 5

| Protein | Residue Number | | | | | | | | | |
|---|---|---|---|---|---|---|---|---|---|---|
| | (26) 1 | (27) 2 | (28) 3 | (29) 4 | (30) 5 | (31) 6 | (32) 7 | (33) 8 | (34) 9 | (35) 10 |
| gD-1 (Predicted) | lys | tyr | ala | leu | ala | asp | ala | ser | leu | lys |
| gD-1 (Edman degrad.) | lys | tyr | ala | leu | ala | x | ala | met | leu | lys |
| gD-2 (Edman degrad.) | lys | tyr | ala | leu | ala | x | x | x | x | lys |
| | (36) 11 | (37) 12 | (38) 13 | (39) 14 | (40) 15 | (41) 16 | (42) 17 | (43) 18 | (44) 19 | (45) 20 |
| gD-1 (Predicted) | met | ala | asp | pro | asn | arg | phe | arg | gly | lys |
| gD-1 (Edman degrad.) | met | ala | x | x | x | arg | x | arg | x | lys |
| gD-2 (Edman degrad.) | met | ala | x | x | x | arg | x | arg | x | arg |
| | (46) 21 | (47) 22 | (48) 23 | (49) 24 | (50) 25 | (51) 26 | (52) 27 | (53) 28 | (54) 29 | (55) 30 |
| gD-1 (Predicted) | asp | leu | pro | val | leu | asp | gln | leu | thr | asp |
| gD-1 (Edman degrad.) | x | leu | x | x | leu | x | x | leu | x | x |
| gD-2 (Edman degrad.) | x | x | leu | x | leu$^a$ | x | x | leu | x | x | x- Not determined
$^a$Result in question

The degradation data indicate that the N-terminal amino acid for both glycoproteins is lysine. Differences were noted in the methionine, arginine, leucine and alanine profiles for gD-1 and gD-2. In each of these cases, however, several residues were present in both glycoproteins and one or more residues was present in one and missing in the other. Thus, for example, in the case of alanine both proteins were found to have alanine

[2-$^{3}$H]-mannose and [$^{35}$S]-cysteine were also used as radioactive probes for sequence analysis of gD-1. For both of these labels, no radioactivity was detected in the first 30 residues. According to the Watson, et al, deduced amino acid sequence for gD-1, the first cysteine would be expected to occur at residue 66 and the first asparagine that has the appropriate sequence (Asn-x-Thr or Ser) to be a glycosylation site would be expected to occur at residue 94. Thus, the negative data of the present study correlates with what would be predicted from the sequence of gD-1.

An interesting feature of the predicted amino acid sequence is that there is an asparagine residue close to the N-terminus (residue 40 of the deduced sequence, or residue 15 of the protein). According to the sequence of the adjacent amino acids, this asparagine is not a potential glycosylation site. Since no [2-3H]-mannose label was detected at this position, it appears that this asparagine is not glycosylated in the protein.

The overall conclusion drawn from the above experiments is that gD-1 and gD-2 appear to be quite similar although not identical in sequence in the N-terminal region of the protein. Only one difference (methionine at residue 8) was noted between the Watson, et al, predicted sequence for gD-1 and the actual sequence. Since different strains of HSV-1 were used for the two studies, the data emphasize the overall conservation in sequence of gD between different strains of HSV-1.

The above data concerning the first thirty amino acids in the sequences of gD-1 and gD-2 does not reveal the sequence of any epitope corresponding to a sequence present in the assertedly immunologically active, microbially-expressed "gD-related" polypeptide and fusion polypeptide described in Watson, et al. With the possible exception of residues (52) through (54) in Table 5, none of the predicted amino acids were specified by the expression vectors whose manufacture is therein described. Only the region of the gD-1 coding sequence to the right (i.e., 3') of the PvuII restriction site was used. Nonetheless, the 30 amino acid sequence was reviewed for the presence of a potential type-common epitope. Analysis by the Hopp, et al, method (supra) showed 3 to 4 hydrophilic regions. Analysis by the method of Chou, et al, (supra) showed 2 potential "bends" in the projected secondary structure of the sequence. One of the projected bends corresponded to one of the hydrophilic sequences in the region spanning amino acid residues 11 through 15 [(36) through (41) of the putative sequence] shown in Table 5. This sequence includes arginine, proline, and methionine residues. It has a calculated molecular weight on the order of 600. The sequence therefore appeared to be the sequence previously characterized in tryptic peptide analysis as the "F" fragment which comprises the epitope for the type common Group VII monoclonal antibody.

Based on the above experimental results, synthetic polypeptides were prepared according to the general methods of Merrifield, *J. Am. Chem. Soc.*, 85, pp. 2149–2154 (1963) and tested for immunoreactivity with monoclonal antibody "170" of Group VII. A first (17-mer) peptide synthesized included 16 amino acid residues duplicative of residues 8 through 23 in Table 5 plus a carboxy terminal cysteine. A second (11-mer) product synthesized includes residues 13 through 23 and a C-terminal cysteine. The first polypeptide was immunoreactive with the Group VII monoclonal. The second (which did not include the methionine and alanine residues believed to comprise the "F" fragment) failed to react with the antibody.

Consistent with the in vitro activity findings, an immunization program involving 10 mice has been commenced. Five of the animals have received the 17-mer polypeptide at a dose of approximately 10 micrograms per mouse. The remaining five animals received the 17-mer covalently linked to a carrier protein (KLH). Preliminary data on humoral responses will be available shortly and it is expected that the test animals will develop immune response involving generation of antibodies protective against Herpes simplex virus infection.

Specifically comprehended by the present invention, therefore, are novel polypeptides which substantially duplicate amino acid sequences present in both gD-1 and gD-2, viz., polypeptides of the structure,

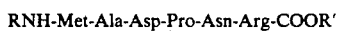

RNH-Met-Ala-Asp-Pro-Asn-Arg-COOR' wherein R is hydrogen or one or more amino acids and R' is hydroxyl or one or more amino acids. A presently preferred polypeptide is that being employed in the immunization procedures described above and having the structure RNH-Ser-Leu-Lys-Met-Ala-Asp-Pro-Asn-Arg-Phe-Arg-Gly-Lys-Asp-Leu-Pro-COOR' wherein R is hydrogen and R' is cysteine. Other presently preferred sequences for polypeptides of the invention include those comprehending the entire gD-1 sequence set out in Table 5, including the species having either methionine or serine at the eighth position. Finally, when the remaining components of the corresponding amino terminal sequence of gD-2 are unambiguously determined, it is contemplated that useful polypeptides will be prepared which include amino acid residues which are present in gD-2 but not gD-1 and especially those residues which have significance to secondary structure of the amino terminal region of the natural glycoprotein gD-2.

As previously indicated, vaccine compositions of the invention may be formulated to include only gD-1 of the invention or only gD-2 of the invention or a mixture of both with an immunologically suitable diluent, adjuvant or carrier. Unit doses including from 0.01 to 10.0 micrograms of purified gD-1 or gD-2 per kilogram of recipient weight are useful in practice of the invention. Total doses of from 0.1 to 100 micrograms are expected to provide an antigenic mass sufficient for practice of protective vaccination procedures of the invention and will result in formation of antibodies corresponding thereto in the host. Due to the lower molecular weight of active polypeptides of the invention (e.g., as few as six amino acids versus a total of over 360 amino acids and carbohydrates) correspondingly smaller amounts of polypeptides may appropriately be employed in vaccines according to the invention.

While the foregoing description of the invention has focused on the utility of immunologically active gD-1 and gD-2 preparations and immunologically active polypeptides as components of vaccine compositions, it will be understood that these preparations will additionally possess utility as components of highly specific diagnostic reagents for detection of Herpes simplex virus antibodies in body fluids including spinal fluids. The specific antigens of the invention (and their biologically active fragments and replicas) may be used to sensitize inert particles of types well known in the art as useful in diagnostic, antigen-antibody reaction detection schemes. In this regard, antigen preparations and antigen-sensitized particles of the invention may be used in combination with suitable "marker" substances (either chemical or radiochemical) in the detection of antibodies by agglutination and radioimmunoassay, as well as fluorescence and enzyme immunoassay, techniques.

Numerous modifications and variations of the above-described invention are expected to occur to those skilled in the art and consequently only such limitations as appear in the appended claims should be placed thereon.

What is claimed is:

1. A diagnostic reagent for use in detection of Herpes simplex virus type 1 antibodies or Herpes simplex virus type 2 antibodies in a fluid sample comprising:

purified and isolated Herpes simplex virus envelope glycoprotein gD-1, purified by selective reversible binding to a monoclonal anti-gD antibody immunoadsorbent, or an immunologically active fragment thereof, or an immunologically active synthetic replica thereof; and, an immunologically acceptable carrier.

2. A diagnostic reagent for use in detection of Herpes simplex virus type 1 antibodies or Herpes simplex virus type 2 antibodies in a fluid sample comprising:

purified and isolated Herpes simplex virus envelope glycoprotein gD-2, or an immunologically active fragment thereof, or an immunologically active synthetic replica thereof; and, an immunologically acceptable carrier.

3. A diagnostic reagent according to claim 1 or 2 comprising a polypeptide having an amino acid sequence selected from the group consisting of:

a) RNH-Met-Ala-Asp-Pro-Asn-Arg-COR', b) RNH-Ser-Leu-Lys-Met-Ala-Asp-Pro-Asn-Arg-Phe-Arg-Gly-Lys-Asp-Leu-Pro-COR', c) RNH-Lys-Tyr-Ala-Leu-Ala-Asp-Ala-Ser-Leu-Lys-Met-Ala-Asp-Pro-Asn-Arg-Phe-Arg-Gly-Lys-Asp-Leu-Pro-Val-Leu-Asp-Gln-Leu-Thr-Asp-COR', and d) RNH-Lys-Tyr-Ala-Leu-Ala-Asp-Ala-Met-Leu-Lys-Met-Ala-Asp-Pro-Asn-Arg-Phe-Arg-Gly-Lys-Asp-Leu-Pro-Val-Leu-Asp-Gln-Leu-Thr-Asp-COR', wherein R is hydrogen or one or more amino acids and R' is hydroxyl or one or more amino acids.

* * * * *